United States Patent [19]

Ullman et al.

[11] 4,046,636
[45] Sept. 6, 1977

[54] DIAZEPAM ENZYME CONJUGATES

[75] Inventors: Edwin F. Ullman, Atherton; Kenneth E. Rubenstein, Menlo Park, both of Calif.

[73] Assignee: Syva Company, Palo Alto, Calif.

[21] Appl. No.: 689,234

[22] Filed: May 24, 1976

Related U.S. Application Data

[60] Continuation-in-part of Ser. No. 481,022, June 20, 1974, abandoned, which is a division of Ser. No. 304,157, Nov. 6, 1972, Pat. No. 3,852,157, which is a continuation-in-part of Ser. No. 143,609, May 14, 1971, abandoned.

[51] Int. Cl.$^2$ .............................................. C07G 7/02
[52] U.S. Cl. ........................... 195/63; 195/DIG. 11; 195/103.5 R
[58] Field of Search ........................ 195/63, DIG. 11

[56] References Cited

U.S. PATENT DOCUMENTS 3,850,752  11/1974  Schuurs et al. ....................... 195/63

*Primary Examiner*—Alvin E. Tanenholtz
*Attorney, Agent, or Firm*—Townsend and Townsend

[57] ABSTRACT

Novel compositions are provided for the determination of one or a group of organic materials (hereinafter referred to as "ligands"), where the compositions have a ligand or ligand counterfeit bonded to an enzyme, the conjugate referred to as "enzyme-bound-ligand." Specifically, the ligands are benzdiazocycloheptane drugs, which are conjugated to an enzyme, so that upon binding of a receptor, usually an antibody, the activity of the enzyme changes. Determinations of the benzdiazocycloheptane drugs in a physiological fluid are performed by combining the enzyme conjugate, the physiological fluid and receptor under conditions whereby the amount of receptor bound to the conjugate is related to the amount of the benzdiazocycloheptane drug present in the sample. By metering the enzyme activity of the assay mixture and comparing the result to known standards, the amount of benzdiazocycloheptane drug present in the sample may be determined.

16 Claims, No Drawings

DIAZEPAM ENZYME CONJUGATES

CROSS-REFERENCE TO RELATED APPLICATIONS

This application is a continuation-in-part of application Ser. No. 481,022, filed June 20, 1974, now abandoned which is a divisional of application Ser. No. 304,157, filed Nov. 6, 1972, now U.S. Pat. No. 3,852,157, which is a continuation-in-part of application Ser. No. 143,609, filed May 14, 1971, abandoned.

BACKGROUND OF THE INVENTION

1. Field of the Invention

There is a continually pressing need for rapid, accurate qualitative and quantitative determinations of biologically active substances at extremely low concentrations. The purpose of the determination can be extremely varied. Today, there is a wide need for determining the presence of drugs or narcotics in body fluids, such as saliva, blood or urine. In addition, in medical diagnosis, it is frequently important to know the presence of various substaces which are synthesized naturally by the body or ingested. These include hormones, both steroidal and polypeptides, prostaglandins, toxins, as well as other materials which may be involved in body functions. Frequently, one is concerned with extremely small amounts and occasionally, with very small differences in concentrations.

To meet these needs, a number of ways have been devised for analyzing for trace amounts of materials. A common method is to use thin layer chromatography (TLC). By determining the flow factors and using specific reagents, the presence of certain materials can be detected; in many instances, the particular material can be isolated and identified quantitatively, for example, by mass spectroscopy or gas phase chromatography. However, thin layer chromatography has a number of deficiencies in being slow, requiring a high degree of proficiency in its being carried out, being subject to a wide range of interfering materials, and suffering from severe fluctuations in reliability. Therefore, the absence of satisfactory alternatives has resulted in intensive research efforts to determine improved methods of separation and identification.

An alternative to thin layer chromatography has been radioimmunoassay. Here, antibodies are employed for specific haptens or antigens. A radioactive analog employing a radioactive atom of high flux is used and bound to the antigen. By mixing an antibody with solutions of the hapten or antigen and the radioactive hapten or antigen analog, the radioactive analog will be prevented from binding to the antibody in an amount directly related to the concentration of the hapten or antigen in the solution. By then separating the free radioactive analog from the antibody bound radioactive analog and determining the radioactivity of the separate components, one can determine the amount of hapten or antigen in the original solution.

The use of radioactive materials is not desirable for a variety of reasons. First, radioactivity creates handling problems and undesirable hazards. Secondly, the preparation of such compounds involves similar hazards, greatly enhanced by the much larger amounts of radioactive materials which are present. Because of their instability, the radioactive materials have only a short life. In addition, the use of radioactive materials requires a license from the Atomic Energy Commission, subjecting the licensee to review by the Commission as to the maintenance of minimum operating standards. These standards may change from time to time, so as to involve added expense and inconvenience to the licensee. Finally, the separation of the bound and unbound radioactive analog is difficult and subject to error. See, for example Abraham, Prelim. Comm., 29, 866 (1969).

Besides the aforementioned materials, assays at extremely low concentrations would be desirable for a variety of pesticides, such as insecticides, bactericides, fungicides, etc., as well as other organic pollutants, both in the air and water. Organic pollutants may be assayed whenever a receptor can be devised and the pollutant is inert to the reagents employed.

2. Description of the Prior Art

Use of radioimmunoassay is described in two articles by Murphy, J. Clin. Endocr. 27, 973 (1967); ibid., 28, 343 (1968). The use of peroxidase as a marker in an immunochemical determination of antigens and antibodies is found in Stanislawski et al., C. R. Acad. Sci. Ser. D. 1970, 271 (16), 1442-5. (C.A. 74 1144 B). See also, Nakane, et al., J. of Histochem. and Cytochem. 14, 929 (1967) and Avrameas, Int. Rev. of Cytology, 27, 349 (1970). A general description of thin layer chromatography for assay may be found in Stahl, Thin Layer Chromatography, Springer Verlag, New York, 1969. See also, Peron, et al., Immunologic Methods in Steroid Determination, Appleton, Century Crofts, New York, 1970.

Also of interest are publications by Van Weemen, et al., FEBS Letters 14, 232 (1971), and Engvall, et al., Immunochemistry, 8, 871 (1971) concerned with immunoassays employing enzymes. See also U.S. Pat. No. 3,654,090. See also, Cinader, Proceedings of the Second Meeting of the Foundation of European Biochemical Societies, Pergamon, Oxford, 1967, vol. II, chapter four.

SUMMARY OF THE INVENTION

Detection of benzdiazocycloheptane drugs is achieved by employing benzdiazocycloheptane derivatives conjugated to enzymes as a reagent in homogeneous enzyme immunoassays. The enzyme-bound-benzdiazocycloheptane undergoes a change in activity when bound to receptor for benzdiazocycloheptane. Normally, there is a reduction in activity due to the binding of antibody to benzdiazocycloheptane conjugated to enzyme. By combining in an aqueous buffered assay medium the sample to be analyzed, receptor, normally antibody, and the enzyme-bound-benzdiazocycloheptane, and determining the enzyme activity in the medium, by comparing the thus determined enzyme activity with known standards, the concentration of the benzdiazocycloheptane in the sample can be determined.

The benzdiazocycloheptane is conjugated to the enzyme by a relatively short chain, frequently to available amino groups on the enzyme by means of a non-oxocarbonyl linkage, including the nitrogen and thio analogs thereof.

DESCRIPTION OF THE SPECIFIC EMBODIMENTS

U.S. Pat. No. 3,852,157, column 2, line 60 to column 21, line 1 and from column 21, line 47 to column 44, line 57 is incorporated herein by reference.

The enzyme conjugates of this invention are benzdiazocycloheptanes bonded to the enzyme either directly by covalent bond or through a linking group of from 1-12 atoms in the chain, more usually of from 1-8 atoms in the chain, and preferably of from about 1-4 atoms in the chain, which are carbon, oxygen, sulfur or nitrogen (either neutral e.g. amido or bonded solely to carbon e.g. tertiary amino). There may be 0-1 site of ethylenic unsaturation as the only aliphatic unsaturation, and preferably saturated. While the chain may be aliphatic, alicyclic, aromatic or heterocyclic, aliphatic chains are preferred. The total number of heteroatoms (chalcogen of from 8-16 atomic number and nitrogen) in the linking group will generally be from 0-4, more usually from 0-2. Not included in the linking group are the atoms naturally present on the benzdiazocycloheptane and the heteroatom of the enzyme. For the most part amido or amidino linkages to the enzyme will be employed, although imine and amino linkages may also be employed.

For the most part, the enzyme-bound-benzdiazocloheptane will have the following formula

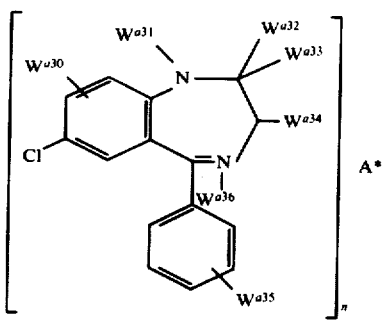

wherein:
anyone of the W groups other than $W^{a36}$ can be —X*;
X* is a bond or linking group as described above bonded to the enzyme at other than its active site;
A* is an enzyme, preferably a hydrolase e.g. lysozyme, or an oxidoreductase, particularly a dehydrogenase e.g. malate dehydrogenase and glucose-6-phosphate dehydrogenase;
n is on the average in the range of from about 1-20, usually 2-12, and more usually from about 2-10, there being a sufficient number of benzdiazocycloheptane groups to provide a significant reduction in activity upon binding of receptor to one or more conjugated benzdiazocycloheptane groups;
when other than X*:
$W^{a30}$ and $W^{a35}$ are hydrogen;
$W^{a31}$ is hydrogen, lower alkyl of from one to three carbon atoms, e.g., methyl, or may be taken together with $W^{a32}$ to from a double bond between the carbon and the nitrogen;
$W^{a33}$ is amino or lower alkylamino of from 1-3 carbon atoms, e.g., methylamino, or may be taken together with $W^{a32}$ to form a carbonyl;
$W^{a34}$ is hydrogen or hydroxyl; and
$W^{a36}$ is oxy or an unshared pair of electrons.
(By active site is intended those amino acid groups which are directly involved in the binding of substrate or occupy the cleft or area to which substrate is bound. In effect, attachment at the particular group will result in substantially total inhibition.)

For the most part, the compounds of this invention will have the following formula

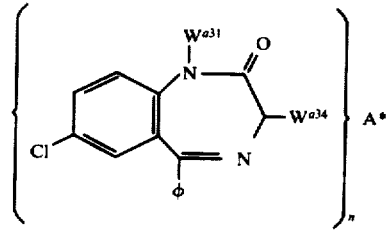

wherein:
anyone of the W groups can be —X*;
A* and n have been defined previously;
when other than X*:
$W^{a31}$ is hydrogen or lower alkyl of from 1-3 carbon atoms, particularly methyl; and
$W^{a34}$ is hydrogen or hydroxyl;
X* is of the formula

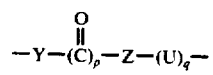

wherein:
Y is oxygen or a bond, being a bond when $W^{a31}$ is X*;
Z is an aliphatic group, usually hydrocarbylene, having from 0-1 site of ethylenic unsaturation as its only unsaturation and of from 1-7, more usually from 1-5 carbon atoms, and from 0 to 1 heteroatom of atomic number 7 to 8 bonded solely to carbon, preferably straight chained alkylene;
U is a bond or a non-oxo-carbonyl group including the nitrogen and sulfur analogs thereof; and
p and q are 0 or 1, the sum of p + q being preferably at least 1. Normally, p is 0 when $W^{a31}$ is X.
(Hydrocarbylene is a divalent radical compound solely of carbon and hydrogen.)

Illustrative groups includes carboxypropylenecarbonyl, oxypropyl, oxybutylcarbonyl, propylenecarbonyl, carboxyethyleneoxyethylenecarbonyl, oxyethyleneimido, succindioyl, and N-methyl 3-azaglutardioyl.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile and hexamethylphosphoramide. The reaction is carried out by bringing the various reagents together under mild conditions and allowing sufficient time for the reaction to occur.

A second method is to form a mixed anhydride employing an alkyl chloroformate, e.g. isobutyl chloroformate. The mixed anhydride is formed by combining the carboxy substituted benzdiazocycloheptane, the alkyl chloroformate and a tertiary amine. The temperature is normally below ambient temperature.

At least a stoichiometric amount of the chloroformate is employed based on the benzdiazocycloheptane derivative, and usually an excess. The excess does not usually exceed three times stoichiometric. The tertiary amine is present in at least equimolar amounts to the chloroformate.

The mixture is then combined with the enzyme to be conjugated and the reaction allowed to proceed under mild conditions.

Also, esters of the carboxy modified benzdiazocycloheptane can be employed which are operative in water for acylating amine functions. An illustrative hydroxylic group is p-nitro-phenol which can be used to prepare the p-nitrophenyl ester.

Finally, imidate esters may be employed under mild conditions at neutral or mildly basic pH in aqueous solvent

EXPERIMENTAL (The following examples are offered by way of illustration and not by way of limitation. All temperatures not indicated are in Centigrade.)

EXAMPLE 1

Oxazepam Hemi-succinate

Oxazepam (2g, 7mmole) and succinic anhydride (1.2g, 11.2 mmole) in pyridine (40 ml, dried over barium oxide) were heated under a nitrogen atmosphere at 95° for 7 hours. The mixture was cooled, and the pyridine removed at reduced pressure. The residue was taken up in ethyl acetate and extracted into aqueous potassium carbonate, pH 13. After neutralizing the basic extracts with aqueous acid, the hemi-succinate was extracted into ethyl acetate, and the extracts washed with saturated brine. They were then dried, filtered, and concentrated in vacuo to give 2,1 g (78%) of the crystalline hemi-succinate, which was recrystallized from ethyl acetate-cyclohexane: m.p. 204°–206° (lit. 204.5°–205.5°).

EXAMPLE 2

Oxazepam Hemi-succinate/BSA Conjugate

Oxazepam hemi-succinate (250 mg, 0.65 mmole) dissolved in dimethylformamide (3.7 ml, dried over molecular sieves) and cooled to −15° under a nitrogen atmosphere, was treated successively with triethylamine (72 mg, 0.71 mmole) and isobutylchloroformate (98 mg, 0.71 mmole). After 2 hours, the mixture was added dropwise to a solution of bovine serum albumin (BSA) (735 mg) in distilled water (150 ml) at 0°. The pH was maintained at 9.5 with 0.05N sodium hydroxide. After 3 hours, sodium bicarbonate (500 mg) was added and the mixture stirred in the cold overnight. 1N Hydrochloric acid was added to reach pH 7.0, the mixture centrifuged at 12000 rpm for 10 minutes, and the supernatant dialyzed against water. Lyophilization of the dialysate gave 700 mg of the conjugate, whose hapten number was found by UV (max at 343 nm) to be 17.5.

EXAMPLE 3

Oxazepam Hemi-succinate Conjugate to Lysozyme

Into a reaction flask was introduced 20.4 mg (5.04 × $10^{-2}$ mmoles) of oxazepam hemi-succinate, 1 ml dimethylformamide and 15μl of triethylamine and the mixture cooled to −15°. Isobutyl chloroformate (6.94μl, 5.3 × $10^{-2}$ mmoles) is added, the mixture stirred for 45 minutes, while the temperature is allowed to rise to −5°.

This mixture is then added to a solution of 120 mg (0.84 × $10^{-2}$ mmoles) of lysozyme in 10 ml water, pH 8.7, at 4°, the pH being adjusted with 0.05N sodium hydroxide. During the addition the pH is maintained at 8.7 and the reaction allowed to continue until the pH is constant for about 30 minutes. The pH is then adjusted to 7.0, the product centrifuged and dialyzed against pH 6.0 0.025M Trismaleate buffer.

EXAMPLE 4

3,7-Dichloro-5-phenyl-1,3-dihydro-2H-1,4-benzodiazepine-2-one

Oxazepam (1.0 g) was added in portions to 1.0 ml of freshly distilled thionyl chloride that contained ∼50μl of DMF with stirring under $N_2$ atmosphere at ice-bath temperature. As soon as the oxazepam was added to the thionyl chloride, the color turned bright yellow and remained unchanged. After complete addition, the heterogeneous reaction mixture was stirred at 0° for 1 hour and then left in the cold room at ∼4° for 24 hours. Excess thionyl chloride was removed on a rotary evaporator. The resulting bright yellow solid was thoroughly mixed with a small amount of anhydrous benzene and then benzene was removed on a rotary evaporator, this was repeated several times to remove thionyl chloride. The residue was then triturated with 3 ml of anhydrous benzene and filtered with suction. The product was dried under vacuum to give 1.1 g of bright yellow solid, m.p. 139°–140° C decomposition (lit. m.p. 151°–153° dec. and 120°–122° C).

EXAMPLE 5

7-Chloro-5-phenyl-3-(ω-hydroxyalkoxy)-1,3-dihydro-2H-1,4-benzodiazepine-2-one

A. 3,7-Dichloro-5-phenyl-1,3-dihydro-2H-1,4-benzodiazepine-2-one (1.0 g) was added in portions to ethylene glycol (60 ml, dried over molecular sieves 5A) with vigorous stirring at room temperature under $N_2$atmosphere. After complete addition the reaction mixture was stirred at room temperature for 4 hours. (Reaction was monitored by TLC and was found to be almost instantaneous.) The reaction mixture was diluted with ∼200 ml of water and extracted with 2 × 150 ml chloroform, the extract dried over anhydrous $Na_2SO_4$ and evaporated on rotary evaporator to give an almost colorless solid (1.05 g; 97%) m.p. 210°–212° C.

A part of the material was recrystallized from acetone to give colorless crystalline solid, m.p. 216° C.

B. Preparation of ω-hydroxypropoxy was carried out in the same way as 2-hydroxyethoxy above by using 1,3-propanediol instead of ethylene glycol. The crude product contained some 1,3-propanediol which went into chloroform along with the product, and this could be removed by triturating the residue with anhydrous ether. Ether dissolved all the contaminated propane diol and a small amount of the product. The alcohol product was obtained as an almost colorless solid, m.p. 177–80° C in 60% yield. A part was recrystallized from acetone to give colorless crystalline solid, m.p. 190° C.

C. The experimental and work up procedures for the preparation of the ω-hydroxybutoxy were exactly the same as above except that 1,3-propanediol was substituted with 1,4-butanediol. The product was isolated as a colorless crystalline solid, m.p. 169°–170° C in 60% yield. A recrystallized sample from acetonitrile melted at 176° C.

EXAMPLE 6

7-Chloro-5-phenyl-3-(ω-carboxyalkoxy)-1,3-dihydro-2H-1,4-benzodiazepine-2-one

The experimental conditions and the work up procedure for the oxidation of all the above three alcohols were identical, therefore the details of the oxidation of only the 2-hydroxyethoxy compound is described:

A. The alcohol (Ex. 5A) (0.5 g) was dissolved in 125 ml of purified acetone (distilled over $KMnO_4$) with slight warming and cooled to 0° in an ice-bath under $N_2$. Jones' chromate reagent (8 ml) was added in four portions with vigorous stirring. The reaction mixture was stirred at 0° for 1 hour and then brought to room temperature and left for an additional hour, and finally poured into 500 ml of ice-cold water and extracted with 3 × 125 ml ethyl acetate. The ethyl acetate extracts were combined and extracted with 3 × 150 ml 5% sodium bicarbonate solution. The bicarbonate solution was carefully acidified to pH 3.0 with 1:1 dil. HCl at 0° and extracted with 4 × 125 ml ethyl acetate. The combined ethyl acetate extracts were dried over anhydrous $Na_2SO_4$, and removal of the solvent on rotary evaporator gave a pale yellow crystalline solid in 65% yield, m.p. 205° C. On recrystallization from acetonitrile, the m.p. rose to 220°. (Lit. m.p. 205°–207° C.)

B. The 2-carboxyethoxy acid was prepared in 77% yield by the oxidation of Ex. 5B (3-hydroxypropoxy). It was recrystallized from acetonitrile to give colorless crystals, m.p. 240°–1° C.

C. Jones' oxidation of the 4-hydroxbutoxy alcohol of Ex. 5C gave in 70% yield the 3-carboxypropoxy acid. It was recrystallized from acetonitrile using a small amount of decolorizing carbon, m.p. 229° dec.

EXAMPLE 7

Carboxypropyloxazepam conjugate to Lysozyme

Into 0.65 ml dry DMF was dissolved the carboxypropyloxazepam prepared in Ex. 6C with agitation and 6.5 ml triethylamine added while maintaining the flask sealed with a serum stopper. The flask contents were cooled to −10°, 5.05µl isobutyl chloroformate added and the mixture stirred for 20 min at −10°. Into 7.75 ml distilled water was dissolved 0.155 g lysozyme with stirring and the solution cooled to 0°–4°. The pH was adjusted to 9.00±0.05 using 0.2N sodium hydroxide at which time the mixed anhydride solution was added dropwise over a period of about 15 minutes with continued stirring followed by allowing the reaction to continue for 2 hours, while maintaining the temperature and the pH with 0.2N NaOH or 0.2N HCl during the entire time. The pH was then adjusted to 7.5 with dropwise addition of 0.2N HCl, followed by centrifugation at 12,000 rpm for 15 min at 4°. The supernatant was placed in a dialysis bag and dialyzed against pH 6.0 tris-mal buffer (0.025 M). The precipitant was suspended in 8M urea, the mixture centrifuged at 12,000 rpm for 15 min at 4° and the supernatant transferred to a dialysis bag and dialyzed as before. The dialysis and urea suspension may be repeated as many times as useable product is obtained in the supernatant.

EXAMPLE 8

Conjugation of 7-chloro-5-phenyl-1-(3'-carboxypropyl)-3-hydro-2-H-1,4-benzodiazepine-2-one with proteins illustrated by bovine gamma globulin A. A mixture of ethyl 4-bromobutyrate, 50ml of acetone and 12.7g of sodium iodide was gently refluxed for 4 hours, then cooled to room temperature and filtered. The clear filtrate was poured into 100ml of ether to precipitate out the inorganic material, and the residue was washed with ether. The combined ether solutions were washed with 1% sodium thiosulfate solution when it turned colorless. After washing once with water, the ether solution was dried over anhydrous $Na_2SO_4$ and the solvent removed under reduced pressure. The residual pale yellow liquid was distilled to give 12.5 g (79%) of the product, b.p. 83°–84° at 4 mm. (Lit. b.p. 84°–85°/4 mm).

B. Des-N-methyldiazepam (450 mg; 1.6 mmole) was dissolved in 4.0 ml of anhydrous DMF under argon, cooled to 0°, and sodium methoxide solution (3.5 ml 1.0 M; 3.5 mmole) was added. The reaction mixture was stirred at 0° for 1 hour and at room temperature for 1 hour, cooled to 0° and a solution of ethyl 4-iodobutyrate (774mg; 3.2mmole) dissolved in 1.0ml of anhydrous DMF added dropwise. After stirring at 0° for 1 hour, the reaction mixture was then brought to room temperature and after three days had only gone to ~50% to completion. An additional amount (774mg; 3.2mmole) of ethyl 4-iodobutyrate was added, and the reaction mixture was stirred at room temperature for 24 hours but no further reaction was noticed.

Most of the solvent was removed under vacuum and the semi-solid residue was dissolved in 1:1 methylene chloride: methanol (40ml) and washed twice with 20ml of water. After drying over anhydrous $Na_2SO_4$, the solvent was removed under reduced pressure to give a pale yellow oil. The product was separated from the starting material by preparative thin layer chromatography (silica gel and 10% MeOH/CHCl_3), which gave 250mg (39%) of the product 1 and 200mg of the starting material.

C. The ester 1 (250mg; 0.65mmole) was dissolved in 1.0ml of methanol and treated with a 2.0 N NaOH solution in 1:1 MeOH/H_2O (0.8ml; 1.6mmole). The reaction mixture turned clear from turbid in a few minutes. It was left at room temperature for 3 hours and then diluted with 6.0ml of water and extracted with 2 × 5ml of methylene chloride. The methylene chloride extract was discarded. The aqueous solution was carefully acidified at 0° with dilute HCl and then extracted with 3 × 8ml methylene chloride. After drying over anhydrous $NA_2SO_4$, the solvent was removed under reduced pressure to give a pale yellow semi-solid material which turned into a foam under vacuum (205mg; 89%). The yellow color could not be removed on treatment with activated charcoal. The product 2 was re-crystallized from methanol as a colorless crystalline material (102mg; 45%) m.p. 168°–169°.

D. The acid 2 (50mg; 0.15mmole) was dissolved in 1.5 ml of anhydrous DMF and cooled to −10° while protecting it from the moisture by using a Drierite tube. After the temperature was equilibrated, the drying tube was replaced by a rubber septum. Triethylamine (15.7mg; 21.5µl; 0.155mmole) was added through a syringe with stirring and after a few minutes, isobutyl chloroformate (21.1mg; 21μl; 0.155mmole) was added through a syringe. The reaction mixture was stirred at −8° to −12° for 2 hours.

In a separate flask bovine gamma globulin (BgG) (400mg; 0.19mmole) was dissolved in 30ml of water and its pH was adjusted to 9.5 with 0.05 N NaOH. The solution was cooled to 0° in an ice-bath. The mixed anhydride solution was added dropwise to this solution with stirring. The reaction mixture turned milky. The pH of the reaction mixture dropped very slowly and was controlled at 9.5 by adding 0.05 N NaOH. It took about three hours for the pH to stabilize. The reaction mixture turned clear on stirring at 4° overnight. The clear solution (pH 9.0) was dialyzed against 0.1M NaHCO$_3$ (4l) when a thick precipitate separated out. The bicarbonate solution was replaced by dilute ammonium hydroxide solution (pH 10,4l) and dialyzed overnight during which time the precipitate dissolved and the solution turned clear. The ammonia solution was changed four times and the last time it was dialyzed overnight. It was filtered through a micropore filter (0.45) under pressure into a sterilized flask and lyophilized to give 350mg of white fluffy solid.

The hapten number of the conjugate was determined by its U.V. The conjugate did not show clear maxima at 310 mμ due to BgG absorption. In view of this difficulty, the extinction coefficient of BgG alone was determined under the same conditions at 310 mμ. The hapten number was calculated by using the following equation:

$$n = \frac{W(\epsilon_{BgG\ 310\ m\mu}) - X(\text{mole.wt. of } BgG)}{X(\text{mole.wt. hapten}) - W(\epsilon_{hapten\ 310\ m\mu})}$$

$n$ = hapten number
$W$ = weight of conjugate (gm/l)
$X$ = optical density of conjugate at 310 mμ
$\epsilon$ = extinction coefficient $$n = \frac{1.46(30188.7) - 0.97 \times 150,000}{0.97 \times 356.5 - 1.46 \times 2130} = 36.7$$

Following substantially the same procedure, enzymes could be conjugated with 7-chloro-5-phenyl-1-(3'-carboxypropyl)-3-hydro-2-H-1,4-benzodiazepine-2-one.

Antibodies were prepared employing the conjugate of Example 2 in accordance with known procedures. Sheep were injected with 1ml of a solution of 30mg/ml of the conjugate in 4 sites, with complete Freund's adjuvant and the injections repeated approximately on a monthly basis using incomplete Freund's adjuvant, with bleeds carried out one week after the injection. The second bleed was harvested and the antibodies isolated according to known techniques.

The following is the procedure employed for the determination of the presence of Librium, Valium, and Oxazepam.

In carrying out the assay, a number of reagent solutions are prepared:

A. Buffer solution: Tris-maleate, 0.55m, pH 6.0;
B. Bovine serum albumin solution: 0.1 weight percent BSA in Tris-maleate prepared above;
C. Bacteria: 40mg of M. luteus suspended in 50ml buffer solution. The suspension is prepared daily, 12 hours before use and stored at 4° C;
D. Benzdiazepine-lysozyme (Example 3): the stock solution of benzdiazepine conjugated with lysozyme is diluted with 0.1 weight percent BSA and Tris-maleate (0.025M Tris; pH 6.0) and stored.

The active lysozyme content of the working solution is determined by measuring at 436nm the rate of bacteriolysis at 30°. The assay solution is prepared by mixing 0.2mg bacteria, 0.02ml of 0.1 weight percent BSA-buffer, 0.08ml synthetic urine (or urine where appropriate) and 0.50ml of the lysozyme solution. The antibody is employed in 0.025M Tris-maleate (pH 7.4) at a concentration suitable for 20μl to inhibit >85 percent of the benzdiazepine-lysozyme activity of the stock enzyme solution. The stock enzyme solution should provide about 150 OD units from a sample having no benzdiazepine to a sample where the benzdiazepine saturates the available antibody binding sites. (OD units are optical density units on a U.V. spectrometer at the measurement temperature.)

To prepare synthetic urine, 5.2g potassium chloride, 8.2g sodium chloride, 1.4g sodium dihydrogenphosphate, 1.4g disodium monohydrogenphosphate, and 11g of urea are combined in one liter of distilled water.

In carrying out the assay, 20μl of the antibody solution is added to 0.2ml of the bacterial suspension. To this solution is added 80μl of urine and the mixture diluted with ½ ml of the enzyme solution. The mixture is then aspirated into the spectrometer and the decrease in optical density is measured at 435nm for 40 seconds. The concentration of benzdiazepine in the urine sample is read from a standard curve prepared by using standardized solutions and taking readings.

To demonstrate the sensitivity of the antibodies produced in accordance with this invention, a wide variety of drugs were dissolved in synthetic urine and the concentration required to give the same result as oxazepam in the subject assay determined. The following table indicates the results.

TABLE I

| Compound | Level Equal to 1μg/ml Oxazepam μg/ml |
|---|---|
| Oxazepam | 1.0 |
| N-Desmethyl diazepam | 0.6 |
| Diazepam (Valium) | 2.5 |
| Temazepam | 11.5 |
| Chlordiazepoxide | 17.5 |
| Medazepam | 19.0 |
| Flurazepam | 70.0 |
| Diphenyl hydantoin | 1000 |
| Amphetamine | >1000 |
| Morphine | >1000 |
| Methadone | >1000 |
| Phenobarbitol | >1000 |

When the conjugate of Ex. 7 was employed and cross-reactivity determined, the following results were obtained.

TABLE II

| Compound | Level Equal to 0.7μg/ml Oxazepam μg/ml |
|---|---|
| Oxazepam | 0.7 |
| N-Desmethyl Diazepam | 0.6 |
| Diazepam | 0.8 |
| Temazepam | 1.1 |
| Chlordiazepoxide | 4.5 |
| Medazepam | 2.6 |
| Flurazepam | 65.0 |
| Amphetamine | >1000 |
| Morphine | >1000 |
| Benzoyl ecgonine | >1000 |
| Methadone | >1000 |
| Secobarbitol | >1000 |
| Dextropropoxyphene | >1000 |

It is evident from the above tables that with the exception of flurazepam, which differs substantially from oxazepam in having a fluorine substituent on the phenyl substituent and a large group bonded to the 1-nitrogen, antibodies are able to detect the more common benzdiazepine tranquilizing drugs. And where the drugs have been abused and relatively high levels taken, those drugs such as medazepam and flurazepam would be detectable. Therefore, with the subject assay one is able to make a rapid screen to determine whether one or more popular benzdiazepine tranquilizers has been employed. Where the particular benzdiazepine tranquilizer employed is known, a quantitative or semi-quantitative determination of the benzdiazepine can be made.

In testing various patients known to be taking Librium or Valium, at dosages of 5mg not more than 3 times in a 12 hour period, the values obtained in the urine by the subject assay with the conjugate of Example 3 were below the 1μg/ml value which was used as a cut-off for a positive result. However, with patients receiving 15 to 50mg of the benzdiazepine drug per dose, 35 of 41 urine samples from patients known to be taking benzdiazepine drugs were shown to be positive. However, no information was available as to the period of time between the taking of the drug and the taking of the urine sample.

The results show that the subject assay is effective for determining not only oxazepam, but also Valium and Librium. It should be noted that these compounds are subjected to metabolism and the production of metabolites. Therefore, Valium, Librium and Oxazepam are metabolized to form compounds which together with any unmetabolized benzdiazepine drug is capable of being detected in the subject immunoassay.

The enzyme-bound-benzdiazocycloheptanes are particularly effective for use in immunoassays for the determination of benzdiazepine drugs. Excellent reproducibility is obtained in the assay, as well as high sensitivity. Thus, a convenient and rapid assay is provided for determining benzdiazepine, and particularly metabolites of benzdiazepine in urine.

Although the foregoing invention has been described in some detail by way of illustration and example for purposes of clarity of understanding, it will be obvious that certain changes and modifications may be practiced within the scope of the appended claims.

What is claimed is:

1. An enzyme-bound-benzdiazocycloheptane, wherein said benzdiazocycloheptane is bound to an enzyme at other than its active site and wherein said enzyme retains at least 30% of its original acitivity and has reduced activity when said benzdiazocycloheptane is bound to antibody for said benzdiazocycloheptane.

2. An enzyme-bound-benzdiazocycloheptane of the following formula

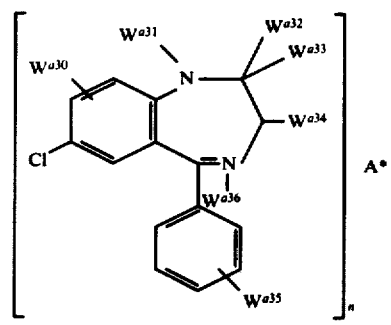

wherein:
any one of the W groups other than $W^{a36}$ can be $-X^*$;
$X^*$ is a bond or linking group bonded to the enzyme at other than its active site;
$A^*$ is an enzyme;
$n$ is on the average in the range of from about 1-20;
when other than $X^*$:
$W^{a30}$ and $W^{a35}$ are hydrogen;
$W^{a31}$ is hydrogen, lower alkyl of from 1-3 carbon atoms, or may be taken together with $W^{a32}$ to form a double bond between the carbon and the nitrogen;
$W^{a33}$ is amino, lower alkyl amino of from 1-3 carbon atoms or may be taken together with $W^{a32}$ to form a carbonyl;
$W^{a34}$ is hydrogen or hydroxyl; and
$W^{a36}$ is oxy or an unshared pair of electrons.

3. An enzyme-bound-benzdiazocycloheptane according to claim 2, $W^{a30}$ and $W^{a35}$ are hydrogen, wherein $n$ is in the range of about 2-12, and $A^*$ is a hydrolase.

4. An enzyme-bound-benzdiazocycloheptane according to claim 2, wherein:
$W^{a30}$ and $W^{a35}$ are hydrogen, $n$ is on the average in the range of from about 2-12, and $A^*$ is an oxidoreductase.

5. An enzyme-bound-benzdiazocycloheptane of the formula

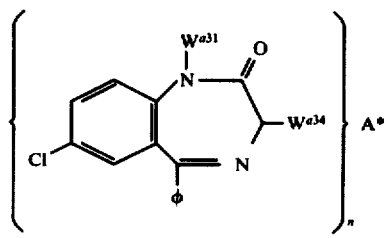

wherein:
anyone of the W groups can be $-X^*$;
$A^*$ is an enzyme;
$n$ is on the average in the range of 2-12;
when other than $X^*$:
$W^{a31}$ is hydrogen or lower alkyl of from 1-3 carbon atoms; and
$A^{a34}$ is hydrogen or hyroxyl;
$X^*$ is of the formula

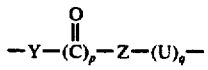

wherein:

Y is oxygen or a bond, being a bond when $W^{a31}$ is X*;

Z is an aliphatic group having from 0-1 site of ethylenic unsaturation as its only unsaturation and of from 1-7 carbon atoms and having from 0-1 heteroatom of atomic number 7-8 bonded solely to carbon;

U is a bond or a non-oxo-carbonyl group including the nitrogen and sulfur analogs thereof; and p and q are 0 or 1.

6. An enzyme-bound-benzdiazocycloheptane according to claim 5, when A* is a hydrolase.

7. An enzyme-bound-benzdiazocycloheptane according to claim 6, wherein said hydrolase is lysozyme.

8. An enzyme-bound-benzdiazocycloheptane according to claim 5, wherein said $w^{a34}$ is X*, Z is aliphatic hydrocarbolene of from 1-5 carbon atoms and A* is a hydrolase.

9. An enzyme-bound-benzdiazocycloheptane according to claim 8, wherein said hydrolase is lysozyme.

10. An enzyme-bound-benzdiazocycloheptane according to claim 5, wherein $W^{a31}$ is X*, Z is aliphatic hydrocarbylene, and A* is a hydrolase.

11. An enzyme-bound-benzdiazocycloheptane according to claim 10, wherein said hydrolase is lysozyme.

12. An enzyme-bound-benzdiazocycloheptane of the formula

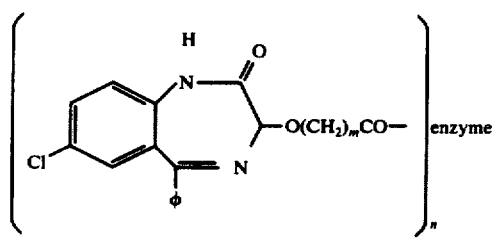

wherein:

m is from 1-3 and n is from about 2-12.

13. An enzyme-bound-benzdiazocycloheptane according to claim 12, wherein said enzyme is lysozyme and m is 3.

14. An enzyme-bound-benzdiazocycloheptane of the formula

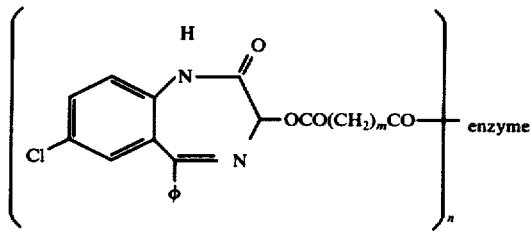

wherein:

m is of from 1-3 and n is of from about 2-12.

15. An enzyme-bound-benzdiazocycloheptane according to claim 14, wherein said enzyme is lysozyme and m is 2.

16. An enzyme-bound-benzdiazocycloheptane of the formula

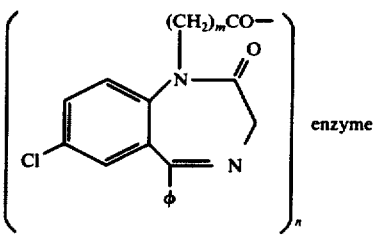

wherein:

m is from 1-3 and n is from about 2-12.

* * * * *